US00PP35309P2

(12) United States Plant Patent
Trees et al.

(10) Patent No.: US PP35,309 P2
(45) Date of Patent: Aug. 8, 2023

(54) ***CLEOME* PLANT NAMED 'BALCLEOLEAM'**

(50) Latin Name: *Cleome hassleriana*
Varietal Denomination: Balcleoleam

(71) Applicant: Ball Horticultural Company, West Chicago, IL (US)

(72) Inventors: Scott C. Trees, Arroyo Grande, CA (US); Colleen N. Konkler, Nipomo, CA (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 18/099,851

(22) Filed: Jan. 20, 2023

(51) Int. Cl.
*A01H 5/02* (2018.01)
*A01H 6/00* (2018.01)

(52) U.S. Cl.
USPC ..... Plt./416

(58) Field of Classification Search
USPC ..... Plt./416
See application file for complete search history.

*Primary Examiner* — Susan McCormick Ewoldt
(74) *Attorney, Agent, or Firm* — Audrey Charles

(57) ABSTRACT

A new and distinct cultivar of *Cleome* plant named 'Balcleoleam', characterized by its deep purple-violet colored flowers, medium green-colored foliage, and moderately vigorous, compact, upright growth habit, is disclosed.

1 Drawing Sheet

Latin name of genus and species of plant claimed: *Cleome hassleriana.*

Variety denomination: 'Balcleoleam'.

BACKGROUND OF THE INVENTION

The present invention relates to a new and distinct cultivar of *Cleome* plant botanically known as *Cleome hassleriana* and hereinafter referred to by the cultivar name 'Balcleoleam'.

The new cultivar originated in a controlled breeding program in Guadalupe, Calif. during August 2018. The objective of the breeding program was the development of *Cleome* cultivars lacky woody thorns and having a compact, upright growth habit.

The new *Cleome* cultivar is the result of cross-pollination followed by embryo rescue. The female (seed) parent of the new cultivar is SEÑORITA ROSALITA 'Inncleosr', U.S. Plant Pat. No. 19,733, characterized by its medium to light purple-colored flowers, medium green-colored foliage, and vigorous, upright and compact growth habit. The male (pollen) parent of the new cultivar is 'White Queen', not patented, characterized by its white-colored flowers, medium green-colored foliage, and moderately vigorous, upright growth habit. The new cultivar was discovered and selected as a single flowering plant within the progeny of the above stated cross-pollination during May 2019 in a controlled environment in Guadalupe, Calif.

Asexual reproduction of the new cultivar by terminal stem cuttings since May 2019 in Guadalupe, Calif. and West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balcleoleam' as a new and distinct cultivar of *Cleome* plant:

1. Deep purple-violet colored flowers;
2. Medium green-colored foliage; and
3. Moderately vigorous, compact, upright growth habit.

Plants of the new cultivar differ from plants of the female parent primarily in having deeper purple-colored flowers, larger diameter inflorescences, and reduced growth vigor. Plants of the new cultivar differ from plants of the male parent primarily in having deep purple-colored flowers unlike the white-colored flowers of the male parent and reduced growth vigor.

Of the many commercially available *Cleome* cultivars, the most similar in comparison to the new cultivar is PEQUEÑA ROSALITA 'Incleninro', U.S. Plant Pat. No. 27,012. However, in comparison, plants of the new cultivar differ from plants of 'Incleninro' in at least the following characteristics:

1. Plants of the new cultivar have slightly darker purple-violet colored flowers than of plants of 'Incleninro';
2. Plants of the new cultivar have smaller compound leaves than plants of 'Incleninro'; and
3. Plants of the new cultivar have smaller flower bracts than plants of 'Incleninro'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balcleoleam'. The plants were approximately 5-months old. The plants were grown in 3-gallon containers for approximately 12 weeks in an outdoor nursery in West Chicago, Ill. Plants were pinched twice prior to transplant.

DETAILED BOTANICAL DESCRIPTION

Figure 1:
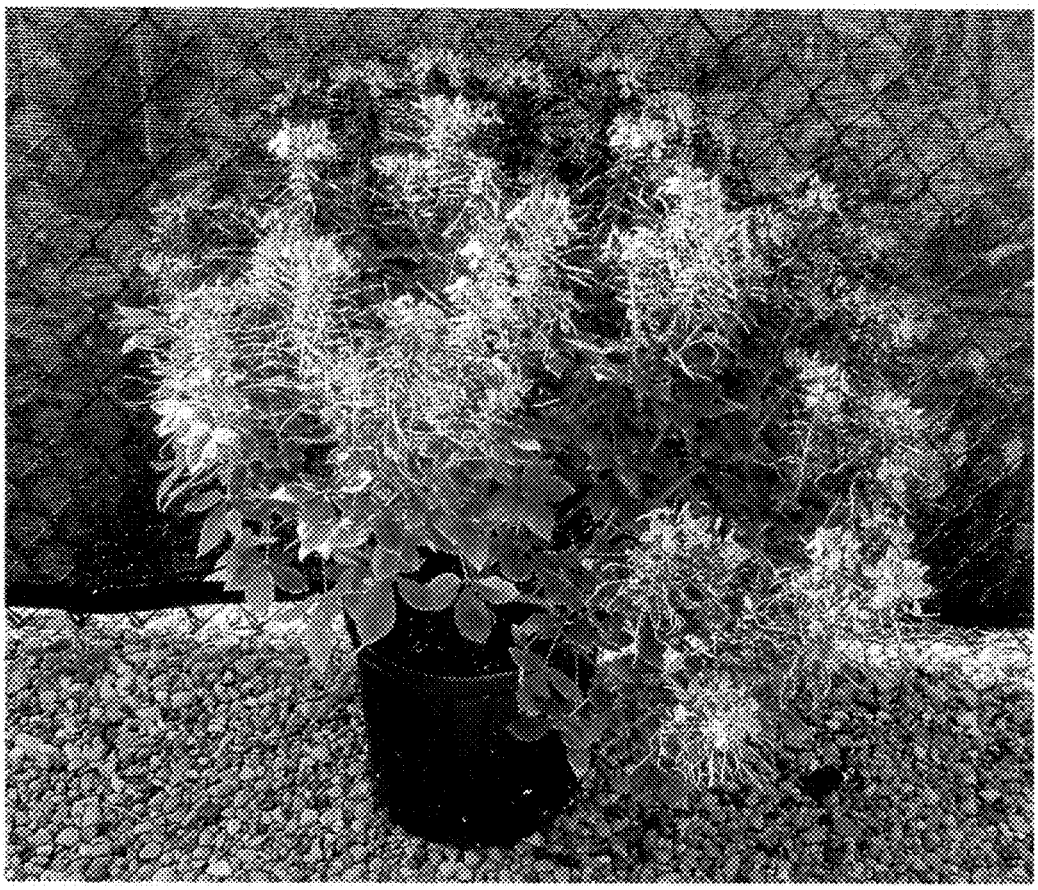
FIG. 1 illustrates a side view of the overall growth and flowering habit of 'Balcleoleam'.
Figure 2:
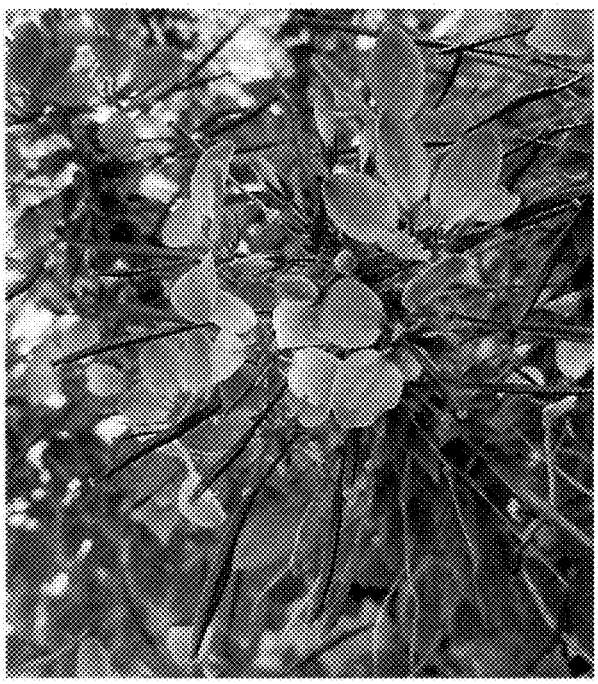
FIG. 2 illustrates a close-up view of an individual inflorescence of 'Balcleoleam'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in August 2022 under natural light conditions in Naperville, Ill.

The following descriptions and measurements describe approximately 5-month-old plants produced from cuttings from stock plants and grown under conditions comparable to those used in commercial practice. The plants were grown in 3-gallon containers for approximately 12 weeks in an outdoor nursery in West Chicago, Ill. Plants were given two pinches prior to transplant. Prior to transplant plants were grown in a polycarbonate greenhouse in West Chicago, Ill. Greenhouse temperatures were maintained at approximately 75° F. to 80° F. (24° C. to 27° C.) during the day and approximately 65° F. to 70° F. (18° C. to 21° C.) during the night. Supplemental lighting was used for first two weeks after sticking. Measurements and numerical values represent averages of typical plants.

Botanical classification: *Cleome hassleriana* 'Balcleoleam'.

Parentage:

*Female parent.*—SEÑORITA ROSALITA 'Inncleosr', U.S. Plant Pat. No. 19,733.

*Male parent.*—'White Queen', not patented.

Propagation:

*Type cutting.*—Terminal stem.

*Time to initiate roots.*—Approximately 10 days.

*Time to produce a rooted cutting.*—Approximately 5 weeks.

*Root description.*—Fine, fibrous.

*Rooting habit.*—Freely branching, moderately dense.

Plant description:

*Commercial crop time.*—Approximately 8 to 10 weeks from a rooted cutting to finish in a 15 cm container.

*Growth habit and general appearance.*—Moderately vigorous, compact, upright.

*Size.*—Height from soil level to top of plant plane: Approximately 61.0 cm. Width: Approximately 93.0 cm.

*Branching habit.*—Freely branching, pinching improves basal branching. Quantity of main branches per plant: Approximately 6.

*Branch.*—Shape: Round in cross section. Strength: Strong, rigid. Length: Approximately 57.0 cm. Diameter: Approximately 6.0 mm to 1.0 cm. Length of central internode: Approximately 3.5 cm. Texture: Densely pubescent with a mixture of glandular and nonglandular hairs. Gland color: Colorless, transparent. Color of young stems: 144A. Color of mature stems: 146B with an overlay of 187A, becomes woody N199A with age.

Foliage description:

*General description.*—Quantity of leaves per main branch: Approximately 13. Fragrance: None detected. Form: Palmately compound with 5 to 3 leaflets per leaf, woody thorns not observed. Arrangement: Alternate.

*Leaves.*—Aspect: Primarily perpendicular or obtuse angle to stem. Overall shape: Obovate. Leaflet shape: Elliptic. Margin: Entire, ciliate. Apex: Acute. Base: Attenuate. Venation pattern: Pinnate, arcuate. Length of mature leaf: Approximately 9.5 cm. Width of mature leaf: Approximately 9.3 cm. Length of center leaflet: Approximately 8.0 cm. Width of center leaflet: Approximately 3.6 cm. Length of lateral leaflet: Approximately 6.0 cm. Width of lateral leaflet: Approximately 3.0 cm. Length of lower leaflet: Approximately 3.5 cm. Width of lower leaflet: Approximately 1.7 cm. Texture of upper and lower surfaces: Moderately pubescent with a mixture of glandular and nonglandular hairs. Gland color: Colorless, transparent. Color of upper surface of young and mature foliage: Closest to 137B with venation of 147B. Color of lower surface of young and mature foliage: Closest to 147B with venation of 147C.

*Rachis.*—Length: Approximately 6.0 cm to 8.5 cm. Diameter: Approximately 2.0 mm. Texture: Densely pubescent with a mixture of glandular and nonglandular hairs. Gland color: Colorless, transparent. Color: 146B tinted with 187A.

Flowering description:

*Flowering habit.*—'Balcleoleam' is freely flowering under outdoor growing conditions with substantially continuous blooming from late spring through late summer and year-round in greenhouse environment.

*Lastingness of individual flower on the plant.*—Approximately 3 to 4 days.

Inflorescence description:

*General description.*—Type: Terminal raceme. Quantity per plant: Approximately 75. Fragrance: Strong musky. Length: Approximately 8.0 cm to 17.0 cm. Width: Approximately 8.5 cm to 11.5 cm. Quantity of fully open flowers per inflorescence: Approximately 3 to 5.

*Peduncles.*—Strength: Strong, rigid. Aspect: Acute angle to stem. Length: Approximately 18.5 cm. Diameter: Approximately 4.0 mm. Texture: Densely pubescent with a mixture of glandular and nonglandular hairs. Gland color: Colorless, transparent. Color: 146B to 146C.

Flower description:

*Type.*—Solitary, zygomorphic.

*Bud.*—Rate of opening: Generally takes 3 to 4 days for bud to progress from first color to fully open flower.

*Bud just before opening.*—Shape: Oblong. Length: 1.5 cm. Diameter: Approximately 4.0 mm. Color of upper surface: N81A to N81B.

*Corolla.*—Shape: Rotate with petals positioned primarily on one half. Aspect: Facing upright and outward. Width: Approximately 3.2 cm by 2.5 cm. Depth: Approximately 8.0 mm.

*Petals.*—Quantity: 4 in a single whorl. Shape: Elliptic. Margin: Entire. Apex: Rounded. Base: Clawed. Length: Approximately 2.0 cm including an approximately 4.0 mm claw. Width: Approximately 1.0 cm and claw of approximately 1.0 mm. Texture of upper and lower surfaces: Glabrous. Color of upper surface when fully open: N81A to N81B with NN155D at base of blade and claw of N81B. Color of lower surface when fully open: NN155D with an overlay of N81C.

*Calyx.*—Shape: Star. Diameter: Approximately 1.7 cm.

*Sepals.*—Quantity per flower: 4. Shape: Lanceolate. Margin: Entire. Apex: Acute. Base: Truncate. Length: Approximately 7.0 mm. Width: Approximately 1.5 mm. Texture of upper (inner) surface: Glabrous. Texture of lower (outer) surface: Densely glandular pubescent. Gland color: Colorless, transparent. Color of upper (inner) surface: 137A with an overlay of 187A. Color of lower (outer) surface: 137A with a heavy overlay of 187A.

*Bracts.*—Quantity per flower: 1, subtending each flower. Shape: Cordate. Apex: Acute. Base: Cordate. Length: Approximately 1.3 cm. Width: Approximately 8.0 mm. Texture of upper and lower surfaces: Densely glandular pubescent. Gland color: Colorless, transparent. Color of upper surface: 137A. Color of lower surface: 137C.

*Pedicels.*—Strength: Strong, rigid. Aspect: Acute angle. Length: Approximately 1.7 cm. Diameter: Approximately 1.0 mm. Texture: Densely glandular pubescent. Gland color: Colorless, transparent. Color: 187A.

*Reproductive organs.*—Androecium: Stamen quantity: 6 per flower. Filament length: Approximately 2.0 mm. Filament color: 146D with N81A. Anther shape: Linear. Anther length: Approximately 5.0 mm. Anther color: 15B. Pollen amount: None observed. Gynoecium, persistent, held on a gynophore (stalk): Pistil quantity: 1 per flower. Pistil length including gynophore: Approximately 1.9 cm. Stigma shape: Capitate. Stigma length: Approximately 1.0 mm. Stigma color: N81A. Style length: Approximately 1.0 mm. Style color: N81A, darkens to 187A with age. Ovary length: Approximately 7.0 mm. Ovary color: N81A, darkens to 187A with age. Gynophore length: Approximately 1.1 cm. Gynophore diameter: Approximately 1.0 mm. Gynophore color: N81A, darkens to 187A with age.

Seed and fruit production: Neither seed nor fruit production has been observed.

Disease and pest resistance: Resistance to pathogens and pests common to *Cleome* has not been observed.

What is claimed is:

1. A new and distinct cultivar of *Cleome* plant named 'Balcleoleam', substantially as herein illustrated and described.

* * * * *